US012144102B2

(12) United States Patent
Bourne

(10) Patent No.: US 12,144,102 B2
(45) Date of Patent: Nov. 12, 2024

(54) WAVEGUIDE FOR A LINEAR ACCELERATOR AND METHOD OF OPERATING A LINEAR ACCELERATOR

(71) Applicant: Elekta Limited, Crawley (GB)

(72) Inventor: Duncan Bourne, Sussex (GB)

(73) Assignee: Elekta Limited, Crawley (GB)

( * ) Notice: Subject to any disclaimer, the term of this patent is extended or adjusted under 35 U.S.C. 154(b) by 364 days.

(21) Appl. No.: 17/594,705

(22) PCT Filed: Apr. 24, 2020

(86) PCT No.: PCT/EP2020/061474
§ 371 (c)(1),
(2) Date: Oct. 26, 2021

(87) PCT Pub. No.: WO2020/216908
PCT Pub. Date: Oct. 29, 2020

(65) Prior Publication Data
US 2022/0201833 A1 Jun. 23, 2022

(30) Foreign Application Priority Data
Apr. 26, 2019 (GB) ..................................... 1905853

(51) Int. Cl.
*H05H 9/04* (2006.01)
*H01P 7/06* (2006.01)
(Continued)

(52) U.S. Cl.
CPC ............... *H05H 9/042* (2013.01); *H01P 7/06* (2013.01); *H05H 7/16* (2013.01); *H05H 7/22* (2013.01);
(Continued)

(58) Field of Classification Search
CPC ....... H05H 7/18; H05H 7/16; H05H 2007/122
See application file for complete search history.

(56) References Cited

U.S. PATENT DOCUMENTS 2,582,186 A 1/1952 Ernest
4,746,839 A * 5/1988 Kazusa .................... H05H 9/04
315/5.46
(Continued)

FOREIGN PATENT DOCUMENTS

GB 2566118 A 3/2019
JP 06349599 A 12/1994
(Continued)

OTHER PUBLICATIONS

"International Application Serial No. PCT/EP2020/061474, International Search Report dated Jul. 30, 2020", (Jul. 30, 2020), 4 pgs.
(Continued)

*Primary Examiner* — Patrick C Chen
(74) *Attorney, Agent, or Firm* — Schwegman Lundberg & Woessner, P.A.

(57) ABSTRACT

Disclosed herein is a waveguide for use in a linear accelerator. The waveguide comprises cells arranged to receive a beam of charged particles therethrough along a particle path, and is configured to receive an electromagnetic field from a source of electromagnetic radiation. A plurality of the cells are individually switchable cells, with each individually switchable cell comprising a respective switch configured to adjust the supply of electromagnetic radiation to the individually switchable cell.

18 Claims, 3 Drawing Sheets

(51) Int. Cl.
  *H05H 7/12*   (2006.01)
  *H05H 7/16*   (2006.01)
  *H05H 7/22*   (2006.01)
  *A61N 5/10*   (2006.01)
  *H05H 7/00*   (2006.01)

(52) U.S. Cl.
  CPC .......... *A61N 5/10* (2013.01); *H05H 2007/007* (2013.01); *H05H 2007/122* (2013.01); *H05H 2007/225* (2013.01)

(56) References Cited

U.S. PATENT DOCUMENTS

| | | |
|---|---|---|
| 5,497,050 A | 3/1996 | Cheo |
| 2011/0006708 A1* | 1/2011 | Ho .......................... H05H 9/04 315/505 |
| 2014/0185775 A1 | 7/2014 | Tang et al. |
| 2015/0359080 A1 | 12/2015 | Dolgashev |
| 2016/0014876 A1 | 1/2016 | Tantawi et al. |

FOREIGN PATENT DOCUMENTS

| | | | |
|---|---|---|---|
| WO | WO-0111928 A1 | 2/2001 | |
| WO | WO-2011109668 A2 | 9/2011 | |
| WO | WO-2019043070 A2 * | 3/2019 | ............... H05H 7/18 |
| WO | WO-2019142389 A1 | 7/2019 | |

OTHER PUBLICATIONS

"International Application Serial No. PCT/EP2020/061474, Written Opinion dated Jul. 30, 2020", (Jul. 30, 2020), 6 pgs.
"United Kingdom Application Serial No. 1905853.6, Search and Examination Report mailed Feb. 1, 2021", (Feb. 1, 2021), 5 pgs.

* cited by examiner

WAVEGUIDE FOR A LINEAR ACCELERATOR AND METHOD OF OPERATING A LINEAR ACCELERATOR

PRIORITY APPLICATIONS

This application is a U.S. National Stage Filing under 35 U.S.C. § 371 from International Application No. PCT/EP2020/061474, filed on Apr. 24, 2020, and published as WO2020/216908 on Oct. 29, 2020, which claims the benefit of priority to United Kingdom Application No. 1905853.6, filed on Apr. 26, 2019; the benefit of priority of each of which is hereby claimed herein, and which applications and publication are hereby incorporated herein by reference in their entireties.

FIELD

The present disclosure relates to a waveguide for a linear accelerator, a linear accelerator comprising such a waveguide, and a method of operating a linear accelerator.

BACKGROUND

Particle accelerators are used to accelerate charged particles to high speeds. One type of particle accelerator is the linear accelerator ("linac"), which may be used to accelerate charged particles such as electrons along a generally linear acceleration path to relativistic speeds. A linac accelerates particles inside a waveguide, which has a number of cells comprising resonant cavities located along the acceleration path. Electromagnetic waves, typically radio frequency ("RF") waves, are applied to the waveguide and made to propagate down the waveguide. The electromagnetic waves produce an oscillating electromagnetic field in each cavity or cell. It is the action of these electromagnetic fields which causes electrons to be accelerated along the acceleration path. The waveguide is typically configured to first form the electrons into bunches, and then accelerate the electrons down the waveguide in bunches.

Linacs are commonly used in medical applications, for example in the field of radiotherapy. Radiotherapy can be described as the use of ionising radiation, such as X-rays, to treat a human or animal body, and is commonly used to treat tumours within the body of a patient or subject. To produce X-rays for medical use, electrons are accelerated towards a target (e.g. a tungsten target). The electron beam is bent using magnets to direct the beam to the target. The electrons hit the target and x-ray radiation is emitted. The resulting high energy x-ray radiation is then used to treat a patient. Alternatively, in electron beam therapy (EBT), the electron beam itself is used to treat a patient.

It is important for medical applications that the energy of electrons leaving the linac can be closely controlled. In the case of x-ray treatment, the energy (and equivalently frequency) of photons produced when the electrons strike the target is closely related to the energy of the electrons striking the target. Hence, to control the energy/frequency of the photons, the energy of the electrons must be controlled. There is therefore ongoing demand for LINACs in which electron velocity control is improved.

The energy of the therapeutic radiation beam used to treat the patient, whether it be a photon beam or an electron beam, affects the profile of the dose applied to the tumour. The photons or electrons which form the therapeutic radiation beam have a spread of energies, and these particles with various energies will penetrate the patient to differing degrees. It is desirable to produce a beam with a low energy spread for medical (and non-medical) purposes.

Another important factor for medical (and non-medical) applications is that of spot size (otherwise known as beam diameter). In particular, for effective medical treatment, it is desirable for the radiation beam leaving the waveguide to have a small spot size (i.e. small beam diameter). A reduced spot size leads to better control of the energy of the resultant therapeutic radiation beam.

SUMMARY

In a first aspect there is provided a waveguide for use in a linear accelerator, the waveguide comprising cells arranged to receive a beam of charged particles (typically electrons, but optionally another type of charged particles, such as protons, positrons, or molecular ions) therethrough along a particle path (referred to herein as an electron path, where the charged particles used are electrons), the waveguide being configured to receive an electromagnetic field from a source of electromagnetic radiation; wherein a plurality of the cells are individually switchable cells, each respective individually switchable cell comprising a respective switch configured to adjust the supply of electromagnetic radiation to the individually switchable cell (e.g. reduce an amplitude of the electromagnetic radiation supplied to the individually switchable cell).

In a second aspect there is provided a linear accelerator "linac" comprising the waveguide of the first aspect. The linac of the second aspect comprises a source of electromagnetic radiation configured to supply electromagnetic radiation to the waveguide of the first aspect. The linac may further comprise a source of electrons (e.g. electron gun) configured to supply electrons to the input cell.

Herein, 'electromagnetic field' and 'electromagnetic radiation' are used interchangeably. As the skilled person will understand, they have effectively the same meaning in the context of the present disclosure. In practice, electromagnetic radiation refers to the waves of the electromagnetic field.

The inventors have found that the ability to individually adjust the supply of the electromagnetic field in individual switching cells provides a simple and effective solution for fine-tuning electron energies as they leave a waveguide. For example, reducing the amplitude of the electromagnetic field in a given individually switchable cell may be used to reduce the energy of electrons leaving the waveguide (i.e. relative to the energy of electrons leaving the waveguide if the amplitude of the electromagnetic field were not reduced in the given individually switchable cell). In short, the waveguide of the first aspect, and linac of the second aspect, provide an effective solution for accurately controlling electron energy.

Using the ability to apply electric fields (turn 'on') some cells but not others (turn 'off') the energy of the beam can be altered. Previous methods would require all cells past a certain point to be 'off'. By individually switching cells on and off greater control over the beam size and/or spot size can be achieved leading to a different bunch size at the target for a given energy. Other benefits may be gained from other on/off patterns.

As a further example, even if the amplitude of the electromagnetic field is reduced in two neighbouring individually switchable cells along the electron path, the cells adjacent to the two individually switchable cells (e.g. the preceding cell along the electron path, and the subsequent cell along the electron path) would still provide an influence to maintain electrons in bunches having a small spot size and/or low energy spread. Therefore, it is possible to maintain electrons in well-controlled bunches by not setting all cells after a certain point along the electron path to the same, reduced, amplitude of electromagnetic field (which would cause the electron energy spread and spot size to increase as the electrons drift along the electron path to exit the waveguide).

The waveguide may further comprise an input cell for receiving electrons at an input end of the electron path, and an output cell from which electrons can leave the waveguide at an output end of the electron path, wherein the individually switchable cells are positioned between the input cell and the output cell The input cell may be configured to receive electrons from an electron source, and to convey them towards the individually switchable cells. For example, the input cell may have an electron aperture configured for connection to an electron source. The input cell may be supplied with an electromagnetic field and configured to convey electrons from the source and towards the individually switchable cells. The electron source may be an electron gun. The waveguide/linac may comprise an electron aperture between each pair of adjacent cells. The electron apertures may be located along (moreover, may define) the electron path through the cells. In particular, the electron apertures may connect the cells to form the electron path. The output cell may comprise an electron outlet aperture, e.g. through which electrons can leave the waveguide. Accordingly, in use, electrons may travel from the electron source, along the electron path from the input cell to the output cell, and out of the electron output aperture.

The waveguide/linac may further comprise at least one bunching cell between the input cell and the individually switchable cells. The at least one bunching cell may be configured to form electrons into bunches. In some examples, the input cell may also be a bunching cell.

Each cell may comprise a cavity formed therein. The electron path may pass through a centre of each cavity.

Reducing the amplitude of the electromagnetic field in the a given individually switchable cell may be considered as 'switching' the cell. For example, the given accelerating cell may be switchable from a first state, to a second state in which the amplitude of the magnetic field in the given accelerating cell is reduced (i.e. relative to adjacent cells). For example, the amplitude of the electromagnetic field in the given accelerating cell may be suppressed.

The switches may be configured such that the supply of electromagnetic radiation to a first individually switchable cell positioned closer to the input end than the output end of the electron path can be reduced relative to the supply of electromagnetic radiation to a second individually switchable cell positioned between the first individually switchable cell and the output end of the electron path. For example, the individually switchable cells may be configured such that the supply of electromagnetic radiation to each of the individually switchable cells can be individually switched on and off.

In some examples, each switch may be configured such that the electromagnetic field in its respective cell can be reduced to a second amplitude, while the electromagnetic field in the adjacent cells is at a first amplitude, the second amplitude being lower than the first amplitude. The second amplitude may be zero, e.g. substantially zero.

Each cell may comprise a field aperture for connection to an electromagnetic source. Each field aperture may provide an opening through which the electromagnetic field can enter the cell. The field apertures may be connectable in parallel to the electromagnetic source. Therefore, the cells may be connected in parallel to the electromagnetic source (i.e. as opposed to being connected in series to the electromagnetic source). Each field aperture may be laterally spaced from the electron path, e.g. located at a lateral edge of the cell from the electron path.

The field apertures may be part of the switches. In particular, each switch may comprise the field aperture and a valve, each valve optionally being configured to reduce the electromagnetic field entering its respective cell via its respective field aperture. That is to say, each valve may be individually controllable to open (e.g., in some examples, at least partially open), and close, the field aperture to the electromagnetic field. In some examples, each valve may be individually controllable to close (i.e. fully close) the field aperture. The valves may be solenoid valves and/or valves which comprise ferrite material surrounding the apertures. Each Solenoid valve, and/or each valve comprising ferrite material, may operate by establishing a magnetic field in/across its respective aperture, the magnetic field acting to suppress (e.g. substantially suppress) the electromagnetic field in the respective cell, i.e. by affecting the degree to which the RF field can enter the cell through the aperture. Alternatively, each valve may comprise a respective metal bar that is selectively moved across its respective aperture in order to selectively restrict the RF field entering the respective cell through the respective aperture. The metal bar may be moved by an external electromagnetic actuator. Alternatively, the metal bar may be moved by a mechanical actuator, for example a hydraulic or pneumatic actuator that acts on the metal bar from outside of the vacuum environment of the waveguide.

The linac/waveguide may comprise first and second supply channels arranged substantially parallel to the electron path. The cells may be arranged between the first and second supply channels. The first and second supply channels may be configured to supply the electromagnetic field to the cells. The first and second supply channels may be configured to supply the electromagnetic field from a single electromagnetic source. As the reader will understand, the linac/waveguide could include more than two such supply channels, with the supply channels arranged around the cells and substantially parallel to the electron path.

In practice, the first and second channels are themselves waveguides (given that they convey radiation from the source to the cells). But they are referred to herein as channels or RF conduits, in order to clearly distinguish them from the waveguide that comprises the electron path.

In other examples, each supply channel may be configured to supply the electromagnetic field from a respective electromagnetic source.

In other examples, each switchable cell may be coupled to a respective electromagnetic source. In such an arrangement, the solenoid valves may be dispensed with, and instead the respective electromagnetic sources may be individually switched so as to effect individual switching of the individually switchable cells. In other words, each of the respective electromagnetic sources may be selectively turned off, or controlled to selectively supply a reduced amplitude of electromagnetic field to their respective cells.

For example, to switch a single individually switchable cell, the electromagnetic source connected to that particular individually switchable cell could be controlled to supply an electromagnetic field of reduced amplitude (thereby reducing the amplitude of the electromagnetic field in the individually switchable cell); or controlled to supply no electromagnetic field (thereby turning off the electromagnetic field in the individually switchable cell).

Each cell may only include a single aperture and a single valve. For example, the first and second supply channels may alternately supply the electromagnetic field to the cells along the electron path. For example, the first cell along the electron path (e.g. the input cell) may be supplied with the electromagnetic field from the first supply channel; the second cell along the electron path supplied by the electromagnetic field from the second supply channel; the third cell along the electron path supplied by the electromagnetic field from the first supply channel; and so on. In examples where the first and second supply channels are supplied by an electromagnetic field from the same (single) source, the cells would all be supplied with the same electromagnetic field, but via alternating supply channels.

Alternatively, each cell may comprise a first field aperture through which the electromagnetic field can enter the cell from the first supply channel, and a second field aperture through which the electromagnetic field can enter the cell from the second supply channel. A first valve may be controllable to close (e.g. fully close) the first field aperture. A second valve may be controllable to close (e.g. fully close) the second field aperture. For example, each individually switchable cell may include a first switch comprising the first field aperture and the first valve; and a second switch comprising the second field aperture and the second valve. As the reader will understand, each cell could include more than two field apertures (with each field aperture allowing the electromagnetic field to enter the cell from a respective supply channel), each with an associated valve. In other words, each cell could include more than two switches.

The electromagnetic field may be a radio frequency "RF" field.

In a third aspect there is provided a radiotherapy device comprising the linear accelerator of the second aspect.

In a fourth aspect there is provided a method of controlling the waveguide of the first aspect, or of controlling the linac of the second aspect, or of controlling the radiotherapy device of the third aspect. The method may comprise supplying electromagnetic radiation to a first number of cells and to a third number of cells, while restricting the supply of electromagnetic radiation to a second number of cells, the second number of cells being individually switchable cells placed between the first number and the third number of cells along the electron path. The method may further comprise increasing or reducing the amount of the second number of cells by adjusting the supply of electromagnetic radiation to the individually switchable cells, in order to adjust the energy of the electrons exiting the waveguide. The method may further comprise supplying electromagnetic radiation to the first number of cells to accelerate electrons along the electron path; effecting a reduction in, or stopping, the supply of electromagnetic radiation to the second number of cells, into which the accelerated electrons travel; and supplying electromagnetic radiation to a third number of cells to reform the electrons exiting the second number of cells into bunches, and/or to reaccelerate the electrons exiting the second number of cells. The method may further comprise supplying electromagnetic radiation to bunching cells placed before the first number of cells, to form electrons travelling along the electron path into bunches before they enter the first number of cells.

The method may further comprise supplying electrons to the input cell.

The electromagnetic field supplied to the cells may be configured to convey the electrons from the input cell to the output cell along the electron path. For example, the electromagnetic field supplied to the input cell may be configured to convey the electrons to the accelerating cells. The accelerating cells may be configured to accelerate the electrons towards the output cell.

In embodiments in which the linac comprises at least one bunching cell, the bunching cell may be supplied with an electric field configured to convey the electrons towards the individually switchable cells, and further configured to form the electrons into bunches. The field supplied to the individually switchable cells may be configured to maintain the electrons in bunches, in addition to accelerating the electrons.

The method may comprise controlling the valve (e.g. first valve) of a cell to close (e.g. at least partially close, or fully close) the field aperture (e.g. first field aperture) of the cell to the electromagnetic field. As discussed above, closing the field aperture may actually comprise suppressing the passage of the electromagnetic field into the cell by activating a magnetic field at the aperture, e.g. using a solenoid valve.

The method may comprise controlling the first and second valves of a cell (e.g. an individually switchable cell) to close (e.g. at least partially close, or fully close) the first and second field apertures of the cell.

Also disclosed herein is a method of operating a linac comprising multiple cells arranged along an electron path, the method comprising: supplying electromagnetic field to each of the cells; reducing an amplitude of the electromagnetic field in a given individually switchable cell along the electron path, relative to the amplitude of the electromagnetic field in cells adjacent the given individually switchable cell along the electron path.

Reducing the amplitude of the electromagnetic field in the given individually switchable cell may be considered as 'switching' the given accelerating cell.

The electromagnetic field may have a first amplitude in the cells adjacent the given individually switchable cell, and may have a second (reduced) amplitude in the given individually switchable cell. The second amplitude may be zero, e.g. substantially zero.

The electromagnetic field may be supplied to each of the cells at a first amplitude, and the electromagnetic field may be reduced to a second amplitude in the given individually switchable cell.

The second amplitude may be substantially zero.

The electromagnetic field may be reduced in every other cell along the electron path. In other word, the electromagnetic field may be reduced in alternate cells along the electron path. By operating the linac in this way, cells at the first amplitude may be interdigitated by cells at the second amplitude.

The electromagnetic field may be a radio frequency "RF" field.

BRIEF DESCRIPTION OF THE DRAWINGS

Examples of the present disclosure will now will now be described with reference to the accompanying figures, in which.

DETAILED DESCRIPTION

In radiotherapy, radiation is delivered to a patient to damage unhealthy tissue and cells, such as cancerous tumours. Electrons from a linear accelerator (linac) strike a target (e.g. tungsten target), causing the target to emit high energy photons which are directed towards a patient for treatment. It is desirable to be able to accurately control the delivery of the electrons to the target (both in terms of the rate at which the electrons arrive at the target, and the energy that the electrons have when they arrive at the target).

Alternatively, in electron beam therapy, the electrons themselves are used to treat the patient. In this case, it is desirable to be able to accurately control the delivery of the electrons to the patient from the linac (both in terms of the rate at which the electrons arrive at the patient, and the energy that the electrons have when they arrive at the patient).

Figure 1:
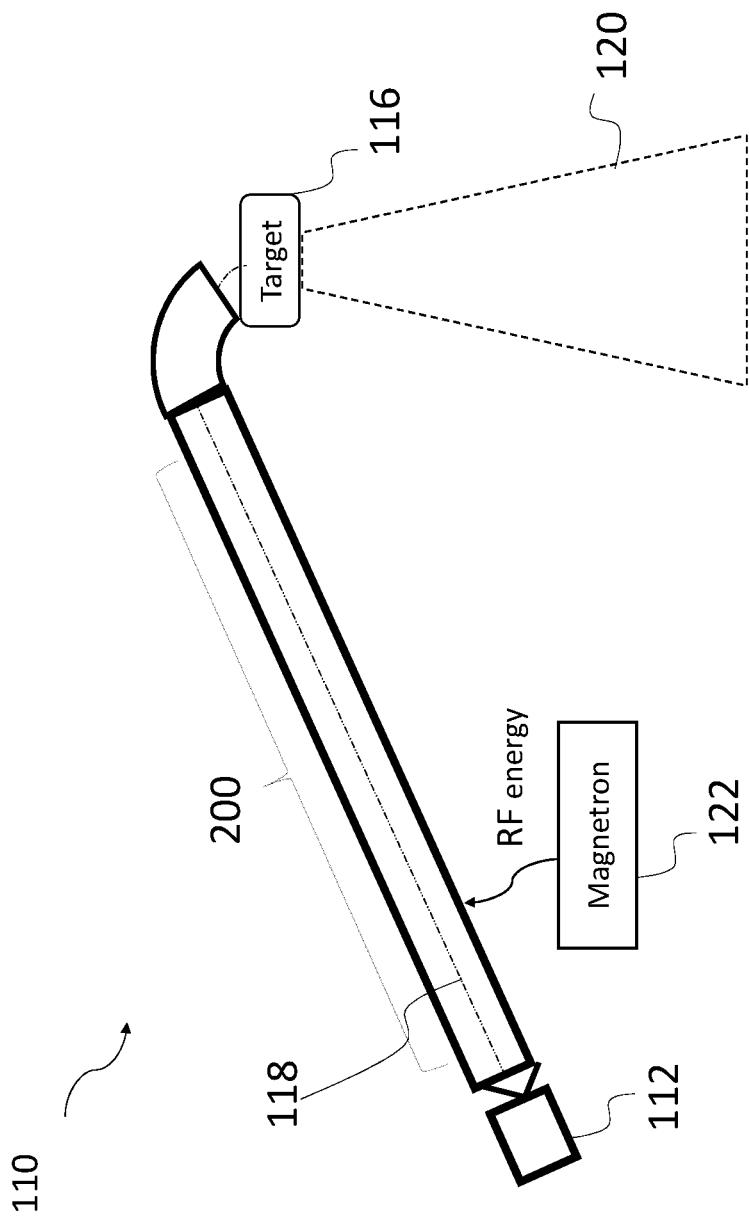
FIG. 1 shows a high-level illustration of a linac for use in radiotherapy.

A high-level overview of a linac according to the present disclosure is illustrated in FIG. 1. The linac 110 includes a source of electrons 112, a waveguide 200 (see FIG. 2), and a target 116. Electrons are emitted from the electron gun and accelerated through the waveguide along an electron path 118 which is coincident with the centre axis of the waveguide. The electron beam is bent using magnets and strikes the target 116, to produce an x-ray beam 120. The x-ray beam 120 is used to treat a patient.

A source 122 (e.g. magnetron) produces an electromagnetic field, e.g. radiofrequency (RF) field. The source 122 is coupled to the waveguide 200, and is configured to pulse the RF field into the waveguide 200.

The source of electrons 112 may be an electron gun. The source of electrons 112 is configured to inject electrons into the waveguide 200. The waveguide 200 comprises a plurality of interconnected acceleration cavities (not shown) forming a channel through which the electron beam passes. The injection of electrons into the waveguide 200 is synchronised with the pumping of the RF field into the waveguide 200.

The design and operation of the source 122, electron source 112 and the waveguide 200 is such that the RF field accelerates the electrons to very high energies as they propagate through the waveguide 200 down the electron path 118. The waveguide 200 is designed in order that a suitable electric field pattern is produced which accelerates electrons propagating through the waveguide 200. To ensure that propagation of the electrons is not impeded as the electron beam travels toward the target, the waveguide 200 is evacuated (i.e. kept under vacuum).

Figure 2:
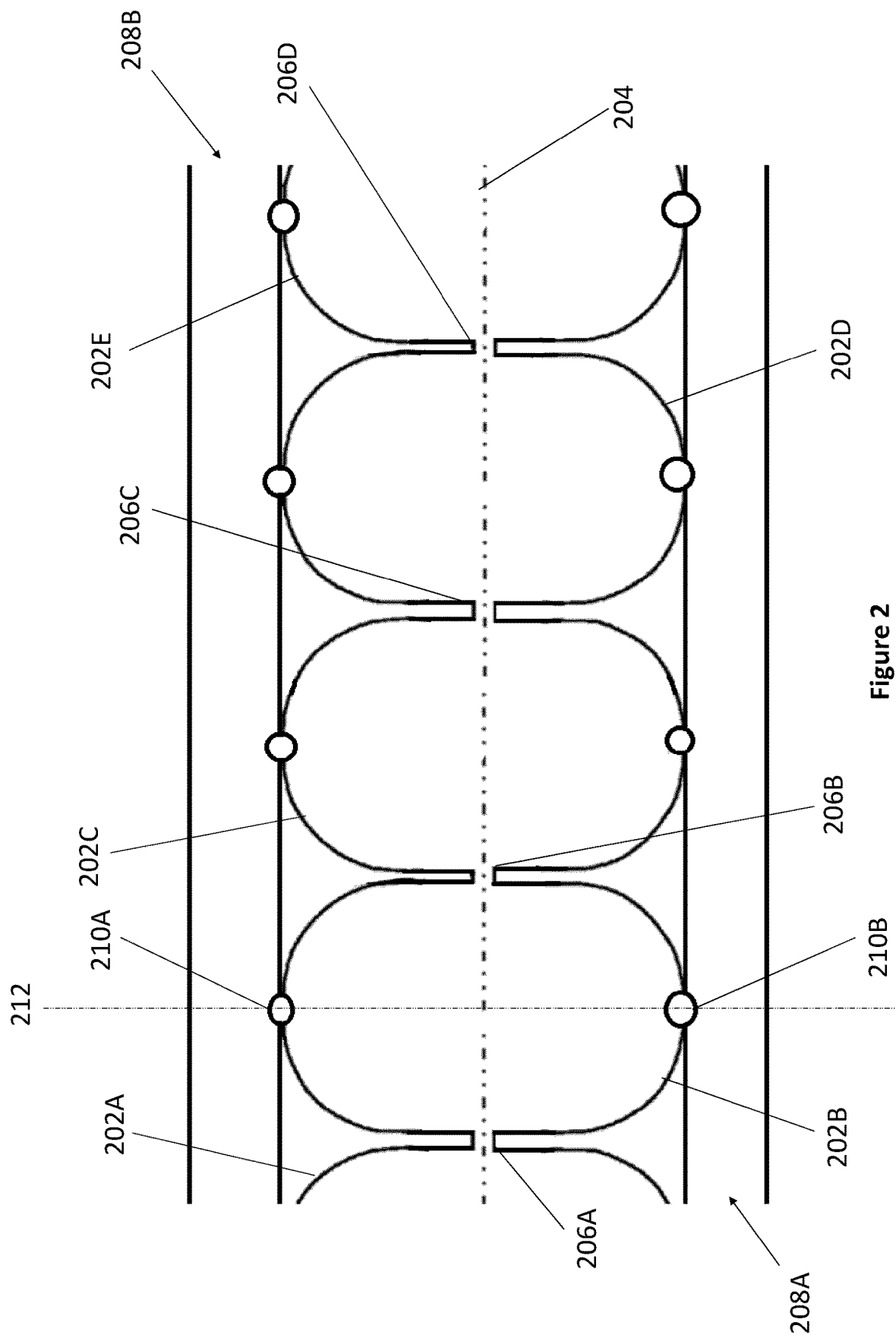
FIG. 2 illustrates an incomplete portion of a waveguide comprising multiple cells arranged along an electron path.

A waveguide 200 for use in a particle accelerator is illustrated in FIG. 2. This is a cross section view along the longitudinal axis of the waveguide 200. This waveguide can be used in a linac as shown in FIG. 1, but also could be used in other accelerators (e.g. a curved accelerator such as a cyclotron or a synchrotron). The below examples and discussion relate to the acceleration of electrons, but the waveguide 200 can be used in the acceleration of any charged particle and therefore in any charged particle accelerator. For example, protons, positrons, and molecular ions, can be accelerated using the techniques described herein.

FIG. 2 illustrates an incomplete portion of a waveguide 200 according to the present disclosure.

The waveguide 200 comprises cavities 202A, 202B, 202C, 202D, 202E arranged along an electron path 204. An electron aperture 206A, 206B, 206C, 206D is located at the interface between each pair of adjacent cavities 202A, 202B, 202C, 202D, 202E. For example, a first electron aperture 206A is positioned at the interface between the cavities 202A and 202B, and a second electron aperture 206B is positioned at the interface between cavities 202B and 202C (and so on). Collectively, the apertures 206A, 206B, 206C, 206D are arranged along the electron path 204. In effect, the apertures 206A, 206B, 206C, 206D define the electron path 204. The electron path 204 extends along a central axis of the waveguide. The apertures and the cavities are centred on the electron path/central axis.

The number of cavities used in a given waveguide will change based on application, design specification etc. Five cavities 202A, 202B, 202C, 202D, 202E are shown in FIG. 2 for illustrative purposes. Each cavity is defined in the form of a recess (not shown) within a surrounding shell of a conductive material, usually copper. Each cavity/recess can be viewed as a region along the electron path for which the separation of the conductive material from the electron path 204 is increased.

The cavities 202A, 202B, 202C, 202D, 202E are manufactured by connecting individual cells together (where each cell comprises a cavity therein). Herein, the terms 'cell' and 'cavity' are sometimes used interchangeably but the above definition holds true. The cells (with cavities therein) are formed by welding segments of conductive material (e.g. copper) together at joining portions 212. The joining portions of the segments are typically in the longitudinal centre of each cell/cavity. A segment will typically form one half of a first cell/cavity, the cell/cavity being mirrored along line 212, and an adjacent half of an adjacent cavity. Multiple segments are welded or brazed together at the joining portions a to form a series of cavities. A single cavity will thus be formed from two separate segments. In the waveguide in FIG. 2, the joining portions are at the longitudinal centre of the cavity.

In use, electrons travel along the electron path 204 from an input cavity (or input cell) 202A, through acceleration cavities 202B, 202C and 202D, to an output cavity (or output cell) 202E.

The input cavity (or input cell) 202A is located at an input end of the electron path 204 and the output cavity (or output cell) 202E is located at an output end of the electron path 204. Individually switchable cells are positioned between the input cell and the output cell. A first individually switchable cavity/cell is positioned closer to the input end than the output end. A second individually switchable cavity/cell is positioned closer to the output end than the input end. The supply of electromagnetic radiation to the first individually switchable cell may be reduced and simultaneously the supply of electromagnetic radiation to a the second individually switchable can be increased.

A first supply channel 208A is provided along a first side of the cavities 202A, 202B, 202C, 202D, 202E, parallel to the electron path 204, and a second supply channel 208B is provided along a second side of the cavities 202A, 202B, 202C, 202D, 202E, also parallel to the electron path 204. The first and second supply channels 208A and 208B are configured to deliver an RF field from a source (not shown) to each of the cavities.

Each cavity receives the RF field from the first supply channel 208A via a first field aperture 210A, and from the second supply channel 208B via a second field aperture 210B. Each of the field apertures is positioned at a lateral edge of the waveguide.

At each first field aperture 210A there is provided a first valve for opening and closing the first field aperture. Collectively, the first field aperture and the first valve form a first switch. At each second field aperture 210A there is provided a second valve for opening and closing the second field aperture. Collectively, the second field aperture and the second valve form a second switch. Typically, the valves are solenoid valves, e.g. solenoid valves comprising ferrite.

Solenoid valves are used to suppress the electromagnetic field in the cavity in question, by establishing a magnetic field in/across the aperture in question (the magnetic field acting to suppress the transmission of the electromagnetic field into the cavity). In another example, each valve comprises a respective metal bar that is selectively moved across its respective aperture in order to selectively restrict the RF field entering the respective cell through the respective aperture. The metal bar is moved by an external electromagnetic actuator, or by a mechanical actuator.

In an alternative example, each cell includes just a single aperture and a single valve. For example, cavity 210A may be connected only to the supply channel 208A by aperture 210B, the aperture 210B being provided with a solenoid valve.

Accordingly, each cavity is directly coupled to the RF source. Moreover, the cavities (cells) are connected in parallel to the RF source via the first and second supply channels 208A, 208B.

Each cavity is individually controllable to have its field apertures 210A, 210B in an open position, a partially closed position, or a fully closed position. In the open position, the valves allow the RF field from the supply channels 208A, 208B to enter the cavity relatively uninhibited such that a maximum amplitude of the RF field is realised inside the cavity. In the partially closed position, the amplitude of the RF field in the cavity is suppressed. In the fully closed position, substantially no RF field enters the cavity, such that the amplitude of the RF field in the cavity is substantially zero.

Because each cavity is individually controllable, a high degree of control of the electrons as they travel along the electron path 204 is realised. For example, in one method of operation of the waveguide, the RF field in cavities 202A, 202C and 202E could be at the maximum amplitude, while the RF field in cavities 202B and 202D is substantially zero.

Electrons travelling along the electron path 204 are accelerated through each cavity 202A, 202B, 202C, 202D, 202E for which an RF field is present. By turning the RF field off in a single cavity, the energy of electrons as they leave the waveguide 200 would thus be reduced slightly. By turning the RF field off in a second cavity, the energy of electrons as they leave the waveguide 200 would be reduced slightly further, and so on. Hence, by having individually controllable cavities 202A, 202B, 202C, 202D, 202E, the energy of electrons leaving the waveguide 200 can be quickly and easily controlled without having to change the RF field being supplied by the source.

Also, because it is possible to (for example) turn the RF field off in every other cavity, a situation in which electrons drift along a downstream portion of the waveguide 200 to the output cavity 202E is avoided. Accordingly, it is possible to ensure that electrons arrive at the output cavity 202E in well-controlled bunches having low energy spread and/or a small spot size.

Moreover, it is possible to reduce the energy of electrons leaving the waveguide 200 as required, without having to change the RF field being supplied by the source, and while still providing electrons to a patient'/target in well-controlled bunches.

In short, the waveguide 200 of FIG. 2 provides for vastly improved electron control.

Furthermore, because the RF field is supplied directly to each cavity 202A, 202B, 202C, 202D, 202E, and coupling of the RF field between adjacent cavities is therefore of less concern (e.g. when compared to waveguides in which the cavities are supplied in series with an RF field), a size of the gap between adjacent cavities can be reduced. This in turn improves electron acceleration thus increasing the maximum electron energy achievable for a waveguide 200 of a given length. This is because the size of the 'dead zones' at the interfaces between cavities is minimised.

Figure 3:
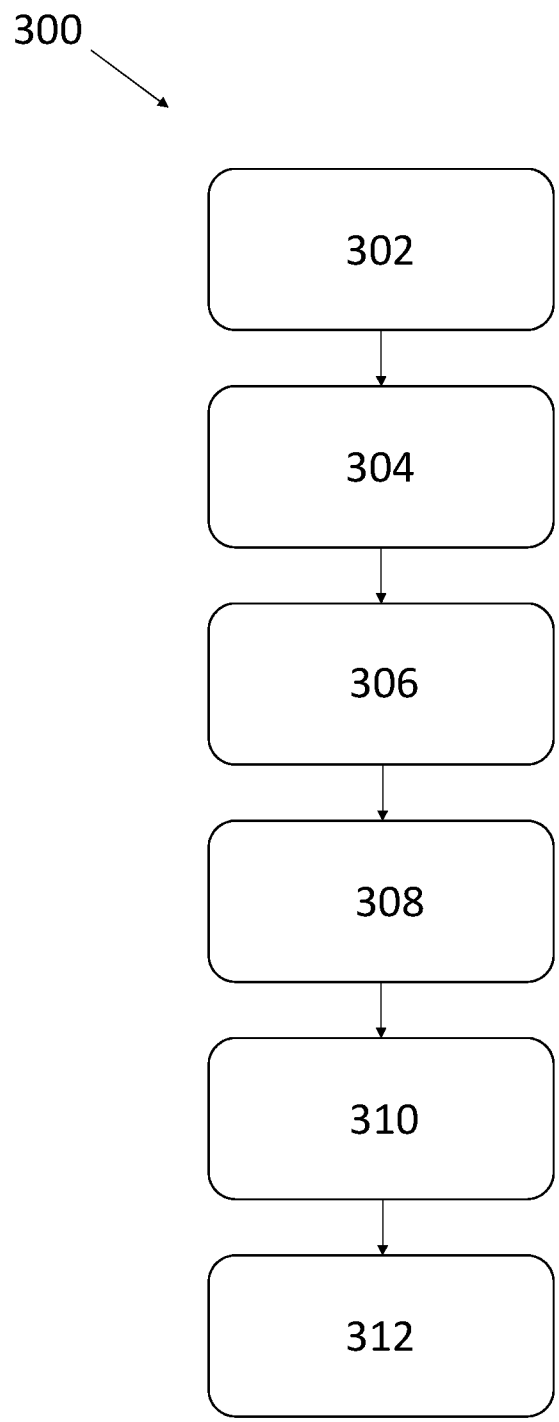
FIG. 3 is a flow diagram illustrates a method of operating a linac, e.g. the linac of FIG. 2.

FIG. 3 is a flow diagram illustrating a method 300 of operating the linac of FIG. 1.

At step 302, the linac 110 is evacuated to remove substantially all air from along the electron path 204.

At step 304, a required electron beam energy for electrons leaving the linac is determined, based on a treatment plan for a particular patient to be treated.

At step 306, a number of cavities 202A, 202B, 202C, 202D, 202E required to achieve the electron beam energy is determined. For example, the number of cavities required to achieve the determined electron beam energy may be five.

At step 308, the cavities 202A, 202B, 202C, 202D, 202E are individually controlled so that the first and second valves (not shown) on five of the cavities are open, and the first and second valves on the remaining cavities are closed. For example, where the waveguide 200 comprises ten cavities, the cavities may be controlled so that the first and second valves of every other cavity are closed, and the remaining valves are open.

At step 310 the RF source 122 is turned on, thereby establishing an RF field in each of the five cavities for which the first and second valves are open. Substantially no RF field exists in the remaining five cavities, because the first and second valves in these cavities are in the closed position.

At step 312 the source of electrons 112 is energised, thereby directing electrons along the electron path 204. These electrons are then accelerated through the waveguide 200 by the RF field, which is present in each of the cavities 202A, 202B, 202C, 202D, 202E for which the first and second valves are in the open position, to an output cavity 202E where the electrons leave the waveguide 200 as an electron beam of the desired energy.

Also disclosed herein is a method of controlling the disclosed waveguide 200, linear accelerator 100 and radiotherapy device. Because the disclosed waveguide 200 comprises cells which are individually switchable, electromagnetic radiation can be supplied, or restricted, to each cell on an individual basis. In an advantageous disclosed method, electromagnetic radiation is supplied to bunching cells, which may be individually switchable cells, in order to form electrons passing through the waveguide 200 into bunches. After the bunched electrons have left the bunching cells, they pass into a first number of cells, which may be called 'accelerating cells'. Electromagnetic radiation is supplied to the first number of cells to accelerate the bunched electrons through the waveguide, along the electron path. After the bunched, accelerated electrons have left the accelerating cells, they pass into a second number of cells. The method then comprises effecting a reduction in, stopping, or restricting the supply of electromagnetic radiation to the second number of cells. As the electrons pass through the second number of cells, they are not accelerated, and so drift along the electron path. The method also comprises supplying electromagnetic radiation to a third number of cells, to again accelerate the electrons which have left the second number of cells.

It is possible to adjust the amount of cells which comprise each 'number of cells' in order to tune the energy of the resulting electron beam. For example, because the cells are individually switchable, it is possible to supply RF to an additional cell, which had previously been part of the 'second number of cells' to which the RF supply had been restricted, so as to increase the number of cells which comprise the 'first number of cells', or the 'accelerating cells'. In other words, by supplying RF to one of the 'second number of cells', i.e. the cells to which the supply of RF is restricted, reduced or halted, it is possible to increase the energy of the resulting electron beam. Vice versa, it is possible to restrict the supply of RF to a cell which had previously been comprised in the 'first number' of cells, and thus reduce the amount of the 'first number of cells' while increasing the number of the 'second number of cells. Thus, the energy of the electron beam which exits the waveguide may be adjusted.

Using the disclosed methods, it is possible to adjust the energy of the electrons exiting the waveguide, and thus, in implementations where the waveguide forms part of a radiotherapy device, adjust the energy of the electron beam or resulting X-rays in treatment, in particular by controlling the number of cells which comprise the 'second number' of cells. In other words, by determining which of the plurality of individually switchable cells should first bunch the electron beam, how many should secondly accelerate the electron beam, and how many should be 'switched off' or otherwise have their supply of RF reduced or restricted, and how many should then 're-form', or 're-accelerate', the electron beam into bunches after they have passed from the cells to which the RF has been restricted, it is possible to provide a waveguide which can provide different beam/electron energies, without causing the electron bunches to have an unacceptably large spread of energies or an unacceptably large spot size when they exit the waveguide. Reference to a 'number of cells' may comprise any number of cells, for example a single cell or a plurality of cells. Any or all of these cells may be individually switchable.

In an example, the method may comprise supplying electromagnetic radiation to a first and a third individually switchable cell, while restricting the supply of electromagnetic radiation to a second individually switchable cell, with the second individually switchable cell being placed between the first and third individually switchable cell along the electron path. This arrangement and method is in complete contrast to currently known waveguides, linacs and currently used methods.

In known arrangements, the cells are not individually switchable, meaning that, to adjust the energy of electrons exiting the waveguide, the only option is to simply 'switch off' the RF supply to a number of cells at the end of the waveguide. Using this known approach, it is possible to provide a waveguide which is capable of producing electron beams of different energies, but these beams are comprised of bunches which have a large spread of energies and a large spot size. In one example known arrangement, a coupling cell is provided between two adjacent cells along the electron path. The coupling cell is controllable, e.g. through the use of a shorting switch, in order to turn the electromagnetic field off in cells downstream of the coupling cell. When the shorting switch is activated, the coupling between the cells either side of it is affected, such that the electromagnetic field is suppressed in all cells downstream of the switching cell. This arrangement does not provide for individual switching of a plurality of individually switchable cells, and further can disrupt the coupling between cells even when the shorting switch is not activated. Travelling through multiple cells in which the RF has been disrupted via the shorting switch leads to the spot size of the beam increasing as it travels.

While reference is made to tuning, or changing, the electron beam energy by changing the number of cells to which RF is restricted or halted, it is also possible to change the beam energy by restricting the RF to these cells to differing degrees, for example by using an RF valve. The valves are individually controllable such that it is possible to at least partially open, and close, a field aperture through which the Rf field enters the individually switchable cells.

The presently disclosed methods may be performed by a processor, or equivalently a controller or computer. The processor may form part of or otherwise be coupled to the radiotherapy device and may be communicatively coupled to each switch of the individually switchable cells. The approaches described herein may be embodied on a computer-readable medium, which may be a non-transitory computer-readable medium. The computer-readable medium carrying computer-readable instructions arranged for execution upon a processor so as to make the processor carry out any or all of the methods described herein.

The term "computer-readable medium" as used herein refers to any medium that stores data and/or instructions for causing a processor to operate in a specific manner. Such storage medium may comprise non-volatile media and/or volatile media. Non-volatile media may include, for example, optical or magnetic disks. Volatile media may include dynamic memory. Exemplary forms of storage medium include, a floppy disk, a flexible disk, a hard disk, a solid state drive, a magnetic tape, or any other magnetic data storage medium, a CD-ROM, or any other optical data storage medium.

It is to be understood that the above description is intended to be illustrative, and not restrictive. Many other implementations will be apparent to those of skill in the art upon reading and understanding the above description. Although the present disclosure has been described with reference to specific example implementations, it will be recognized that the disclosure is not limited to the implementations described, but can be practiced with modification and alteration within the spirit and scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

The invention claimed is:

1. A waveguide for use in a linear accelerator, the waveguide comprising:
   multiple cells arranged to receive a beam of charged particles therethrough along a particle path, the waveguide being configured to receive an electromagnetic field from a source of electromagnetic radiation, wherein a plurality of the multiple cells are individually switchable cells, and wherein each individually switchable cell includes a respective switch configured to adjust a supply of electromagnetic radiation to the individually switchable cell; and
   a first supply channel and a second supply channel arranged substantially parallel to the particle path, wherein each individually switchable cell is arranged between the first supply channel and second supply channel, and wherein the first supply channel and the second supply channel are each configured to supply the electromagnetic radiation to each individually switchable cell.

2. The waveguide of claim 1, the multiple cells further comprising:
   an input cell for receiving a charged particle at an input end of the particle path; and an output cell from which a charged particle can leave the waveguide at an output end of the particle path, wherein the individually switchable cell is positioned between the input cell and the output cell.

3. The waveguide of claim 1, wherein each cell of the multiple cells is an individually switchable cell, and wherein each of the respective switches are configured such that the supply of electromagnetic radiation to a first individually switchable cell positioned closer to an input end of the particle path than an output end of the particle path can be reduced relative to the supply of electromagnetic radiation to a second individually switchable cell positioned between the first individually switchable cell and the output end of the particle path.

4. The waveguide of claim 1, wherein each of the individually switchable cells are configured such that the supply of electromagnetic radiation to each of the individually switchable cells can be individually switched on and off.

5. The waveguide of any of claim 1, wherein each, switch comprises a field aperture and a valve, wherein each valve is individually controllable to open and close the field aperture to the electromagnetic radiation.

6. The waveguide of claim 1, wherein the electromagnetic radiation is radio frequency radiation.

7. A linear accelerator comprising:
a waveguide including:
multiple cells arranged to receive a beam of charged particles therethrough along a particle path, the waveguide being configured to receive an electromagnetic field from a source of electromagnetic radiation, wherein each cell of the multiple cells is an individually switchable cell, and wherein each individually switchable cell includes a respective switch configured to adjust a supply of electromagnetic radiation to the individually switchable cell, and
a first supply channel and a second supply channel arranged substantially parallel to the particle path, wherein each of the individually switchable cells are arranged between the first supply channel and second supply channel, and wherein the first supply channel and the second supply channel are each configured to supply the electromagnetic radiation to each of the individually switchable cells.

8. The linear accelerator of claim 7, wherein the linear accelerator comprises the source of electromagnetic radiation configured to supply electromagnetic radiation to the waveguide.

9. The linear accelerator of claim 7, wherein each respective individually switchable cell comprises a first switch and a second switch, the first switch configured to adjust the supply of electromagnetic radiation supplied to the individually switchable cell from the first supply channel, and the second switch configured to adjust the supply of electromagnetic radiation supplied to the individually switchable cell from the second supply channel.

10. The linear accelerator of claim 9, wherein the first switch comprises:
a first field aperture through which the electromagnetic field enters a particular cell from the first supply channel and a first valve controllable to close the first field aperture to the electromagnetic field; and
a second field aperture through which the electromagnetic field enters a second particular cell from the second supply channel and a second valve controllable to close the second field aperture to the electromagnetic field.

11. The linear accelerator of claim 7, further comprising:
a radiotherapy device.

12. A method of controlling a waveguide, the method comprising:
supplying electromagnetic radiation to a first number of cells and to a third number of cells, while restricting the supply of electromagnetic radiation to a second number of cells, wherein each of the second number of cells are individually switchable cells placed between the first number of cells and the third number of cells along a particle path, wherein a first supply channel and a second supply channel are each configured to supply the electromagnetic radiation to each of the individually switchable cells, wherein the first supply channel and the second supply channel are arranged substantially parallel to the particle path, and wherein each of the individually switchable cells are arranged between the first supply channel and the second supply channel.

13. The method of claim 12, further comprising:
increasing or reducing an amount of the second number of cells by adjusting the supply of electromagnetic radiation to at least one of the individually switchable cells, in order to adjust the energy of the charged particles exiting the waveguide.

14. The method of claim 12, the method comprising:
supplying electromagnetic radiation to the first number of cells to accelerate charged particles along the particle path;
effecting a reduction in, or stopping, the supply of electromagnetic radiation to the second number of cells, into which the accelerated charged particles travel; and
supplying electromagnetic radiation to the third number of cells to reform the charged particles exiting the second number of cells into bunches.

15. The method of claim 12, further comprising:
supplying electromagnetic radiation to bunching cells placed before the first number of cells, to form charged particles travelling along the particle path into bunches before the charged particles enter the first number of cells.

16. A non-transitory computer readable medium comprising computer executable instructions which, when executed by a processor, cause the processor to:
supply electromagnetic radiation to a first number of cells of a waveguide and to a third number of cells of the waveguide, while restricting the supply of electromagnetic radiation to a second number of cells of the waveguide, wherein each of the second number of cells are individually switchable cells placed between the first number and the third number of cells along a particle path, wherein a first and a second supply channel are each configured to supply the electromagnetic radiation to each of the individually switchable cells, wherein the first supply channel and the second supply channel are arranged substantially parallel to the particle path, and wherein each of the individually switchable cells are arranged between the first supply channel and the second supply channel.

17. The non-transitory computer readable medium of claim 16, wherein the instructions further cause the processor to:
increase or reduce an amount of the second number of cells by adjusting the supply of electromagnetic radiation to at least one of the individually switchable cells, in order to adjust the energy of the charged particles exiting the waveguide.

18. The non-transitory computer readable medium of claim 16, wherein the instructions further cause the processor to:

supply electromagnetic radiation to the first number of cells to accelerate charged particles along the particle path;

reduce or stop, the supply of electromagnetic radiation to the second number of cells, into which the accelerated charged particles travel; and supply electromagnetic radiation to the third number of cells to reform the charged particles exiting the second number of cells into bunches.

* * * * *